(12) United States Patent
Colin et al.

(10) Patent No.: US 10,099,220 B2
(45) Date of Patent: Oct. 16, 2018

(54) OBTURATION DEVICE FOR APPLYING A METHOD FOR ISOLATING A SAMPLE WELL OF A TEST CARD FOR ANALYSIS, AND RESULTING TEST CARD AND PROCESSING MACHINING USING THE OBTURATION DEVICE

(71) Applicant: BIOMERIEUX, Mary l'Etoile (FR)

(72) Inventors: Bruno Colin, Marcy l'Etoile (FR); Cecile Paris, Bessenay (FR)

(73) Assignee: BIOMERIEUX, Marcy l'Etoile (FR)

( * ) Notice: Subject to any disclaimer, the term of this patent is extended or adjusted under 35 U.S.C. 154(b) by 119 days.

(21) Appl. No.: 15/140,678

(22) Filed: Apr. 28, 2016

(65) Prior Publication Data

US 2016/0236193 A1 Aug. 18, 2016

Related U.S. Application Data

(62) Division of application No. 13/879,887, filed as application No. PCT/FR2011/052437 on Oct. 19, 2011, now Pat. No. 9,353,398.

(30) Foreign Application Priority Data

Oct. 22, 2010 (FR) ...................... 10 58699

(51) Int. Cl.
  *B01L 3/00* (2006.01)
  *C12Q 1/24* (2006.01)
  *C12Q 1/02* (2006.01)

(52) U.S. Cl.
  CPC ..... *B01L 3/50853* (2013.01); *B01L 3/502738* (2013.01); *C12Q 1/24* (2013.01); *B01L 2200/0689* (2013.01); *B01L 2300/0864* (2013.01); *B01L 2300/0887* (2013.01); *B01L 2400/0481* (2013.01); *B01L 2400/0638* (2013.01); *B01L 2400/0655* (2013.01)

(58) Field of Classification Search
  CPC .... B01L 3/50853; B01L 3/5082; B01L 3/508; B01L 3/502; B01L 3/50; C12Q 1/24; C12Q 1/02
  USPC ................ 422/522, 551, 547, 500
  See application file for complete search history.

(56) References Cited

U.S. PATENT DOCUMENTS

| | | | |
|---|---|---|---|
| 4,121,394 A | 10/1978 | Brooks | |
| 6,128,899 A | 10/2000 | Oono et al. | |
| | (Continued) | | |

FOREIGN PATENT DOCUMENTS

WO 2004/011149 2/2004

*Primary Examiner* — Christine T Mui
(74) *Attorney, Agent, or Firm* — Clark & Brody

(57) ABSTRACT

The invention relates to a method for isolating at least one fluid sample well laid out in a test card for analyses, said test card including a plate (3) having at least one first main face from which is laid out at least one channel communicating with at least said well, this first face being coated with a membrane (17) provided with an adhesive (18) and which will cover said channel with a covering area ($17_1$), the method for isolation including a phase for introducing a fluid sample into at least said well and a phase for isolating said well consisting of exerting a force on at least one portion of the covering area ($17_1$) of the adhesive membrane (17) for ensuring displacement of the adhesive into an obturation area for the sample well.

10 Claims, 4 Drawing Sheets

(56) References Cited

U.S. PATENT DOCUMENTS

| | | | |
|---|---|---|---|
| 7,198,759 B2* | 4/2007 | Bryning | B01L 3/502738 422/504 |
| 8,012,431 B2* | 9/2011 | Cox | B01L 3/502715 422/501 |
| 2004/0157343 A1 | 8/2004 | Sandell | |
| 2004/0195539 A1 | 10/2004 | Mead et al. | |
| 2004/0265180 A1* | 12/2004 | Cox | B01L 3/502715 422/502 |
| 2006/0269451 A1 | 11/2006 | Bedingham et al. | |
| 2007/0059214 A1 | 3/2007 | Cox et al. | |
| 2007/0114229 A1 | 5/2007 | Bedingham et al. | |
| 2008/0112855 A1 | 5/2008 | Lee et al. | |
| 2009/0258415 A1 | 10/2009 | Bryning et al. | |
| 2011/0020179 A1 | 1/2011 | Yue et al. | |
| 2014/0038193 A1* | 2/2014 | Spoto | C12Q 1/686 435/6.12 |

\* cited by examiner

OBTURATION DEVICE FOR APPLYING A METHOD FOR ISOLATING A SAMPLE WELL OF A TEST CARD FOR ANALYSIS, AND RESULTING TEST CARD AND PROCESSING MACHINING USING THE OBTURATION DEVICE

This application is a Divisional of U.S. Ser. No. 13/879,887 filed on Jul. 1, 2013, which is a national phase of PCT/FR2011/052437 filed on Oct. 19, 2011.

The present invention relates to the general technical field of devices and machines for testing biological samples, and more particularly test cards for analysis in which channels are laid out for supplying fluid as far as wells suitable for receiving a reagent and a fluid or test sample containing a microbiological agent such as a microorganism.

The object of the invention more specifically aims at a technique giving the possibility of ensuring obturation of these wells in order to avoid any risk of contamination between these different wells.

In the state of the art, many publications describe various test cards for analysis which have a well or a reaction enclosure designed for receiving a reagent and a fluid sample containing a microbiological agent such as a microorganism. Such a test card which is for example described by patent EP 0 908 728, includes a plate in which are laid out wells communicating with an admission port, via a network of supply channels laid out on either one or on both of the main faces of the plate.

Conventionally, in each of the wells, a reagent is deposited during the manufacturing of the test card. The reagent usually contains a culture medium for a microbiological agent contained in a fluid or test sample. Deposition of a different reagent in each of the wells of the card is thus known for carrying out identification tests on a fluid sample containing a microbiological agent or an unknown organism. The use of the cards for testing the sensitivity of the microbiological agent to antibiotics is also known by depositing various antibiotic reagents in the wells.

In the state of the art, application of a transparent adhesive membrane on either one or on both of the surfaces of the plate is known in order to cover the wells and the fluid supply channels. This transparent adhesive membrane prevents the reagent from being cleared from the well during transport and handling and is also used as a liquid barrier for preventing leakage over the edges of the well of the fluid sample introduced into the well.

It should be considered that there exists a real possibility of fluidic communication between the sample wells during the various steps for processing the test card, which may cause cross-contamination between the various wells. Such a risk is all the more significant since the distance between the wells tends to decrease due to the requirements of laying out a larger number of wells on a test card, the dimensions of which remain identical.

In order to reduce the risk of cross-contamination, the prior art proposed various solutions. For example, U.S. Pat. No. 6,128,899 proposes the filling of the various supply channels via an additional fluid in order to separate the wells from each other. Patent application US 2008/0112855 proposes isolation of the wells from each other by interposing a heat-sensitive obturator allowing the opening or the closing of the supply channels.

It emerges that these techniques for avoiding contamination between the sample wells require modification of the method for manufacturing the test cards by integrating obturation means on the card. These techniques prove to be difficult to apply in practice.

Patent application US 2004/0157343 proposes the closing of the sample wells by locally deforming the test card at right angles to the supply channel. The deformation of the test card is ensured via a heated punch. In practice, this technique is delicate to accomplish insofar that it seems to be difficult to control the temperature and the deformation of the test card. The consequence is a significant risk of degrading the sample wells, which may compromise the integrity of the test process for the microbiological samples.

In the same sense, patent application WO 2004/011149 describes a method and a device for making obturators in a circuit laid out on a substrate. The circuit includes first and second cavities connected together through a channel made in an elastically deformable material. The substrate is covered with an elastically deformable membrane and covering at least the channel in order to delimit communication between the first and second cavities when the membrane is in a non-deformed condition. The method provides deformation both of the membrane and of the material making up the channel by means of specific tools, in order to produce an obturator. According to an alternative embodiment, provision is made for deforming the membrane in order to bring the adhesive layer into contact with the channel in order to ensure obturation between the first and second cavities.

This technique teaches the use of a deformable substrate and of an elastically deformable adhesive membrane, which has a significant risk of degrading the sample wells. Moreover this technique does not undoubtedly ensure isolation of the sample wells.

The present invention therefore aims at finding a remedy to the drawbacks of the state of the art by proposing a novel method for isolating the sample wells of a test card for analyses, this novel method being efficient and simple to apply, while giving the possibility of keeping conventional techniques for manufacturing test cards for analyses.

In order to attain such a goal, the object of the invention relates to a method for isolating at least one fluid sample well made in a test card for analyses, said test card including a plate having at least one first main face from which at least one channel communicating with at least said well is laid out, this first face being covered with a membrane provided with an adhesive and which will cover said channel with a covering area, the method for isolation including:
  a phase for introducing a fluid sample in at least said well,
  a phase for isolating said well, according to an isolation area, consisting of exerting a force on at least one portion of the covering area of the adhesive membrane in order to displace it as far as having it fit the shape of the wall of the channel so as to allow adhesion of said covering area of the adhesive membrane onto the wall of the channel. According to the invention, the method consists of exerting a force on the covering area of the adhesive membrane in order to ensure displacement of the adhesive in an obturation area for the sample well contiguous to the isolation area.

The method according to the invention includes as a combination either one or both of the following features:
  exerting the force on the covering area of the adhesive membrane located overhanging at least one channel for ensuring the displacement of a volume of adhesive, greater than the volume of the obturation area of the channel,
  exerting the force on the covering area of the adhesive membrane located overhanging at least one distribution channel, in order to ensure the displacement of the adhesive in at least one obturation area located in a filling channel communicating between a sample well and the distribution channel, exerting the force on the covering area of the adhesive membrane during a relative displacement between the test card and the pressing member along a direction parallel to the direction of extension of at least one distribution channel in order to ensure the displacement of the adhesive in a filling channel communicating with said distribution channel, exerting a force on the covering area of the adhesive membrane by means of a pressing member having a supporting end with a section mating the section of the channel, exerting a force on the covering area of the adhesive membrane according to a pressure comprised between 0.3 and 0.7 kg/cm$^2$ and preferably of the order of 0.6 kg/cm$^2$, displacing the test card along a direction corresponding to the translational movement of a system for displacing the test card, belonging to a test card processing machine.

Another object of the invention is to propose a novel test card for analyses, with a simple design and providing complete isolation between the sample wells while retaining the integrity of the sample wells.

In order to attain such a goal, the object of the invention relates to a plate having at least one main face from which is laid out at least one channel communicating with at least one sample well, this first face being coated with an adhesive membrane in order to cover said channel with a covering area, at least one portion of the covering area of the adhesive membrane at least locally fits the shape of the wall of the channel, in an isolation area. According to the invention, the test card includes at least one area for obturating the sample wall, adjacent to the isolation area and filled with the adhesive of the adhesive membrane from the obturation area.

Advantageously, the test card according to the invention includes as a combination, either one or both of the following additional features:

at least one obturation area located in a distribution channel, at least at the intersection with at least one channel for filling a sample well, the isolation area adjacent to the obturation area being located in the filling channel, the adhesive membrane is coated with an adhesive having a thickness comprised between 15 and 100 µm, the distribution or filling channel has a section comprised between a semi-circle of height R and with a width equal to 2R on the one hand, and a circular portion with a width √5·R/3 and a height equal to R/3, on the other hand.

Another object of the invention is to propose an obturation device for applying the method according to the invention.

According to this aspect of the invention, the obturation device for applying the method for isolating at least one sample well laid out in a test card for analysis includes a system for exerting a force on at least one portion of the covering area of the adhesive membrane in order to displace it as far as causing it to at least locally fit the shape of the wall of the channel in order to isolate said well with respect to the channel by driving out the adhesive by applying the force on the adhesive membrane.

Advantageously, the obturation device includes either one or both of the following additional features:

the system for exerting a force includes a pressing member with a section mating the section of the channel, the pressing member has a rounded supporting end.

According to a first alternative embodiment, the pressing member is driven for moving closer to/moving away from the test card so as to allow application of at least one portion of the covering area of the adhesive membrane onto the wall of the channel.

According to a second alternative embodiment, the pressing member is mounted so as to be mobile in rotation for rolling on at least one portion of the length of the channel.

Advantageously, another object of the invention is to propose a processing machine including an obturation device according to the invention.

According to a preferred alternative embodiment, the obturation device is mounted so as to act on the test card during a translational movement of conveying means belonging to the processing machine.

Various other features emerge from the description made below with reference to the appended drawings which show, as non-limiting examples, embodiments of the object of the invention.

Figure 1:
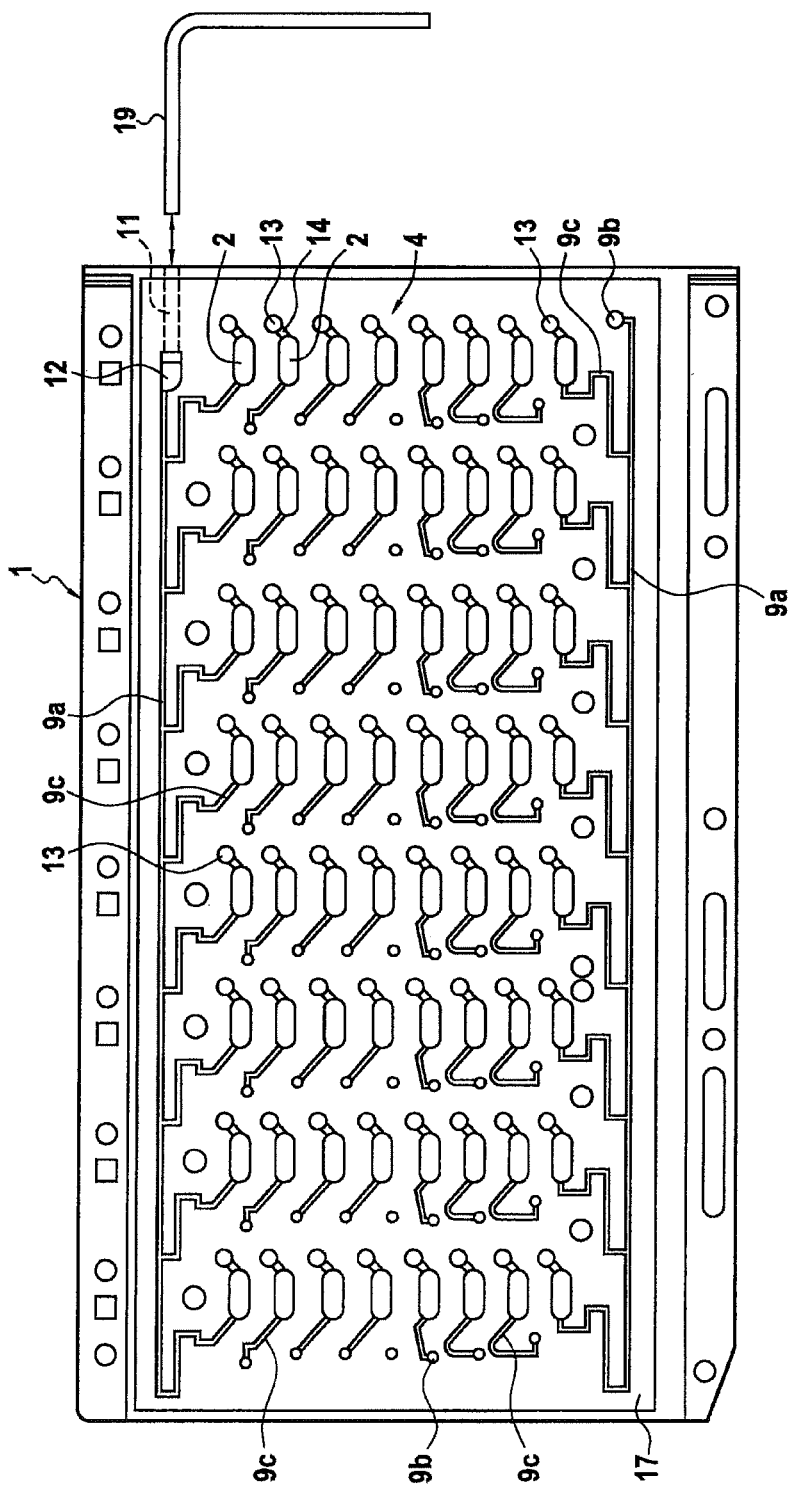
FIGS. 1 and 2 are respectively planar views of the front and rear faces of an exemplary embodiment of a test card applying the method according to the invention.
Figure 2:
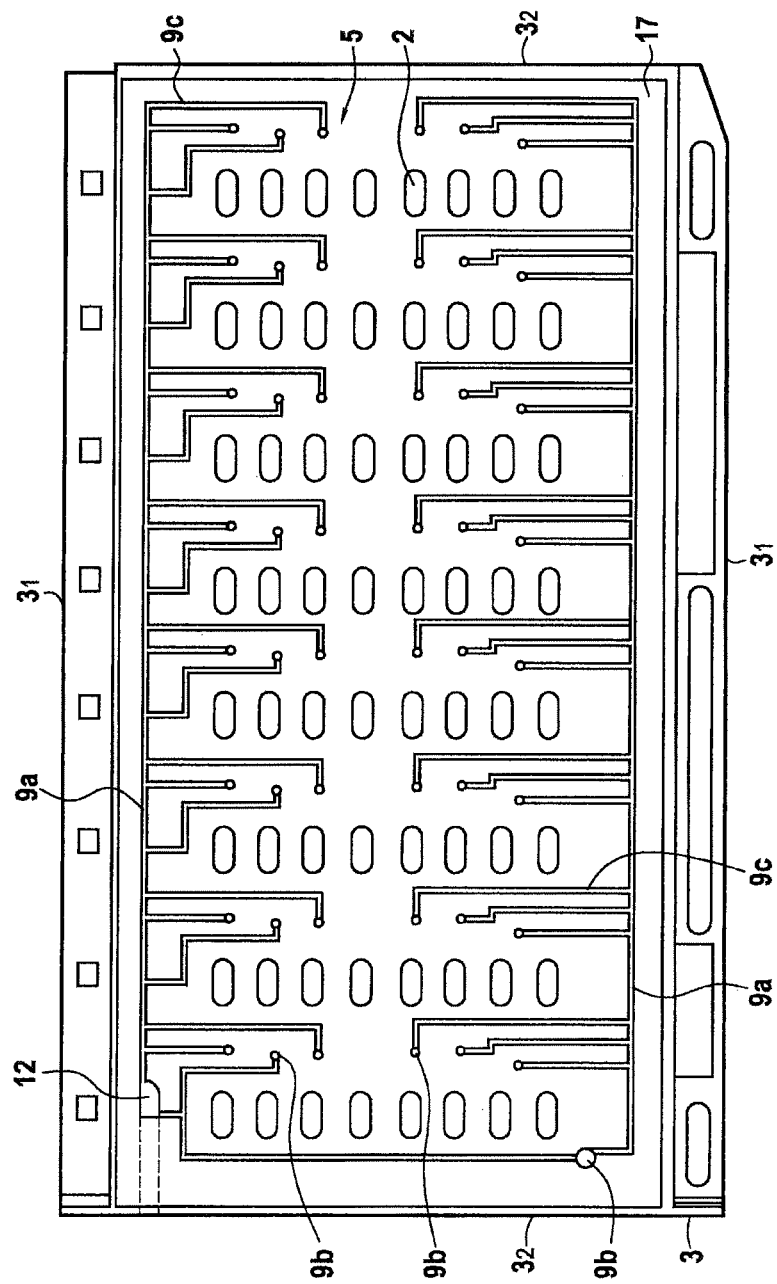

FIGS. 1 and 2 illustrate an exemplary embodiment of a test card 1 including sample wells 2, isolated from each other. Before describing the obturation characteristics of the wells 2, it is recalled that a test card 1 for analysis generally appears as a plate or support 3 with a small thickness having a first so-called main front face 4 and a second so-called rear main opposite face 5. In the illustrated example, the plate 3 has a rectangular shape and has two longitudinal edges 3$_1$ parallel with each other and connected through two transverse edges 3$_2$ also parallel with each other.

This test card 1 includes at least one, and in the illustrated example, a plurality of wells 2 laid out in rows and columns in a preferred embodiment. In the illustrated example, the wells 2 distributed into eight rows and eight columns open out on both faces 4 and 5. Of course, the number, the geometry and the arrangement of the wells 2 may be achieved in a different way. Conventionally, the wells 2 are pre-filled with reagents and/or culture media in order to be able to conduct a biological test on samples.

The test card 1 also includes at least one and generally one network of channels 9a, 9b, 9c laid out in the plate 3 for conveying the fluid sample from a fluid admission port 11 as far as the wells 2. The supply or conveying channels 9a, 9b, 9c are laid out on either one or both of the main faces 4, 5.

These supply channels may be distributed in distribution channels 9a connected to the admission port 11 and on which, filling channels 9c are connected in parallel, each ending up with a well 2.

In the illustrated example, the test card 1 includes fluid distribution channels 9a laid out on the surfaces of the front 4 and rear 5 faces of the plate 3. Advantageously, the portion of the distribution channels 9a to which the filling channels 9c are connected, extend along a direction parallel to the longitudinal edges $3_1$. The distribution channels 9a communicate with each other from one face to the other, by means of connecting channels 9b crossing right through the plate 3. These distribution channels 9a communicate with the admission port 11 via an admission manifold 12.

These distribution channels 9a are connected to the wells 2 via filling channels 9c laid out on both faces 4, 5 of the plate. Each well 2 thus communicates with a distribution channel 9a via one filling channel 9c laid out on one face of the plate or with two filling channels 9c made on both faces 4, 5 and communicating in series by means of a connecting channel 9b crossing right through the plate 3.

According to an alternative, the wells 2 are in communication with bubble traps 13 via passages 14 which allow all the bubbles which may be formed in the well 2 to be directed as far as the corresponding bubble trap 13.

An adhesive membrane 17 is applied on each face 3, 4 of the plate. The adhesive membrane 17 is preferably transparent and includes a support for an adhesive 18. This support which has a thickness comprised between 18 and 100 μm, is for example made with a PMP (polymethylpentene) film having a thickness of the order of 50 μm or with a BOPP (biaxial oriented polypropylene) film with a thickness of the order of 19 μm. This adhesive membrane 17 is conventionally coated with an adhesive 18 having a thickness of the order of 30 μm and preferably comprised between 15 and 100 μm.

This adhesive membrane 17 has an elastic or plastic deformabity. This adhesive membrane 17 has an elongation at break greater than or equal to 160%.

The adhesive membrane 17 thus covers the wells 2 and the channels 9a, 9b, 9c in order to ensure their closing in the plane of the faces 3, 4 of the card. It should be noted that upon applying the adhesive membrane 17 onto the plate 3, the adhesive membrane 17 adheres to the faces 4, 5 without adhering to the walls $9_1$ of the channels 9a, 9b, 9c laid out as recesses from the faces 4, 5 of the plate 3. Thus, the adhesive membrane 17 in particular covers the distribution channels 9a and the filling channels 9c, through a so-called covering area $17_1$. In other words, this covering area $17_1$ corresponds to the portion of the adhesive membrane 17 located facing, overhanging or opposite the distribution channels 9a and the filling channels 9c.

This phase for manufacturing such a test card 1 is not described more specifically insofar that it does not specifically belong to the object of the invention and is well known to one skilled in the art. The manufacturing of such a test card 1 is for example described in more detail in patents U.S. Pat. No. 5,609,928, EP 0 785 433 or EP 0 745 856. Of course, the object of the invention is applied to a test card 1 different from the one described as an example in FIGS. 1 and 2.

During a phase of use, the wells 2 of the test card 1 are filled with a fluid or test sample by means of known techniques for deposition in vacuo. Conventionally, an end of a transfer tube 19 is inserted into the admission port for the fluid 11 and attached into place. The other end of the transfer tube 19 is placed in a receptacle such as a test tube containing the fluid sample. The fluid is drawn off through the transfer tube 19 as far as the admission manifold 12 which supplies the channels 9a, 9b, 9c ensuring transport of the fluid as far as the wells 2.

After this phase for introducing a fluid sample into the wells 2 of the test card 1, the object of the invention is directed to applying a phase for isolating at least one and preferably all the wells 2 of the test card 1 in order to avoid cross-contamination between the wells.

Figure 3:
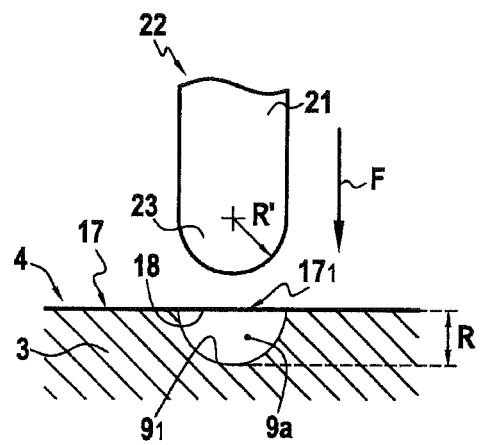
FIGS. 3 to 5 are large scale cross-sectional views of a test card showing three characteristic steps of the method according to the invention, i.e. before applying any force on the adhesive membrane, when applying a force on the adhesive membrane and after suppressing application of a force on the adhesive membrane of the test card, respectively.
Figure 4:
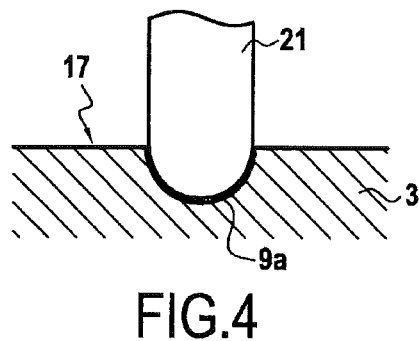
Figure 5:
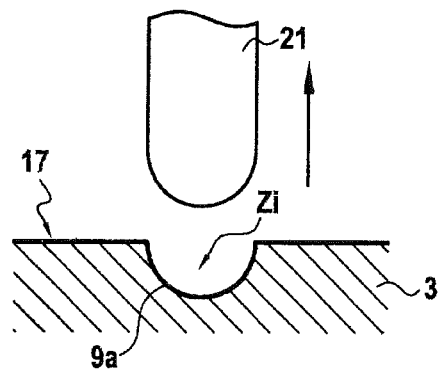

The process or the method for achieving this isolation phase, as this appears more particularly in FIGS. 3 to 5, consists of exerting a force F on at least one portion of the covering area $17_1$ of the adhesive membrane 17, located overhanging or facing at least one channel, which in the drawings is a distribution channel 9a. Of course, applying a force on at least one portion of the covering area $17_1$ of the adhesive membrane 17 located overhanging or facing a filling channel 9c, may be contemplated.

The method according to the invention therefore consists of displacing at least one portion of the covering area $17_1$ of the adhesive membrane 17, in order to cause it to fit the shape of the wall $9_1$ of the channel in order to allow adhesion of this portion of the covering area $17_1$ of the adhesive membrane 17 onto the wall $9_1$ of the channel (FIG. 4). Insofar that this portion of the covering area $17_1$ of the adhesive membrane 17 is brought into contact with the wall of the channel 9a, the adhesive membrane 17 is capable of adhering or remaining adhesively bonded by means of the adhesive 18, to the wall of the channel 9a in an isolation area Zi (FIG. 5). It should be noted that the adhesive membrane 17 is brought into contact with the wall of a channel, without deformation of the support 3.

The application of a force F on the covering area $17_1$ of the adhesive membrane 17 in order to cause it to adhere to the wall of a channel may be ensured by any suitable technical means. In the exemplary embodiment illustrated in FIGS. 3 to 5, the covering area $17_1$ of the adhesive membrane 17 is displaced by means of a pressing member 21 which is part of an obturation device 22. The pressing member 21 includes a supporting end 23 having a section mating the section of the channel.

In the example illustrated in FIGS. 3 to 5, the distribution channel 9a has a semi-circular cross-section of radius R. Thus the distribution channel 9a has a height or depth R and a width equal to 2R.

The pressing member 21 also has a supporting end 23 with a semi-circular section of radius R'. Of course, the pressing member 21 is placed relatively to the channels so as to obtain congruence between the sections of the channel and of the supporting end 23.

Advantageously, the supporting end 23 of the pressing member 21 has a radius R' equal to the radius R of the channel, reduced by the thickness of the adhesive membrane 17. The pressing member 21 ensures drawing or deformation of the adhesive membrane 17 in its covering area $17_1$ in order to bring it into contact with the wall of the channel in order to allow the adhesive 18 to adhere to the wall of the channel.

It should be noted that the pressing member 21 has a supporting end 23 with a general rounded shape in order to avoid piercing the adhesive membrane 17. Thus, as this is apparent from FIG. 6, the pressing member 21 has a rounded section in a plane parallel to the extension direction of the channel.

According to a preferred alternative embodiment, the pressing member 21 exerts on the adhesive membrane 17, a pressure comprised between 0.3 and 0.7 kg/cm$^2$ and preferably of the order of 0.6 kg/cm$^2$.

In the illustrated exemplary embodiments, each channel has a semi-circular cross-section. Of course, the channels may have sections with a different shape. Thus, provision may be made for making a channel with a section comprised between a semi-circle of height R and of width 2R on the one hand and a circular portion of width $\sqrt{5}\cdot R/3$ and of height equal to R/3 on the other hand. Typically, in the case of a channel with a semi-circular section, the radius R of the channel is comprised between 50 µm and 2.5 mm and preferably between 150 µm and 500 µm.

In the example illustrated in FIGS. 3 to 5, the application of the supporting force F on the covering area $17_1$ of the adhesive membrane 17 is obtained by ensuring a relative closing-in movement between the supporting member 21 and the test card 1. After adhesion of the adhesive membrane 17 on the wall of the channel, the pressing member 21 and the test card 1 are moved away from each other.

Figure 6:
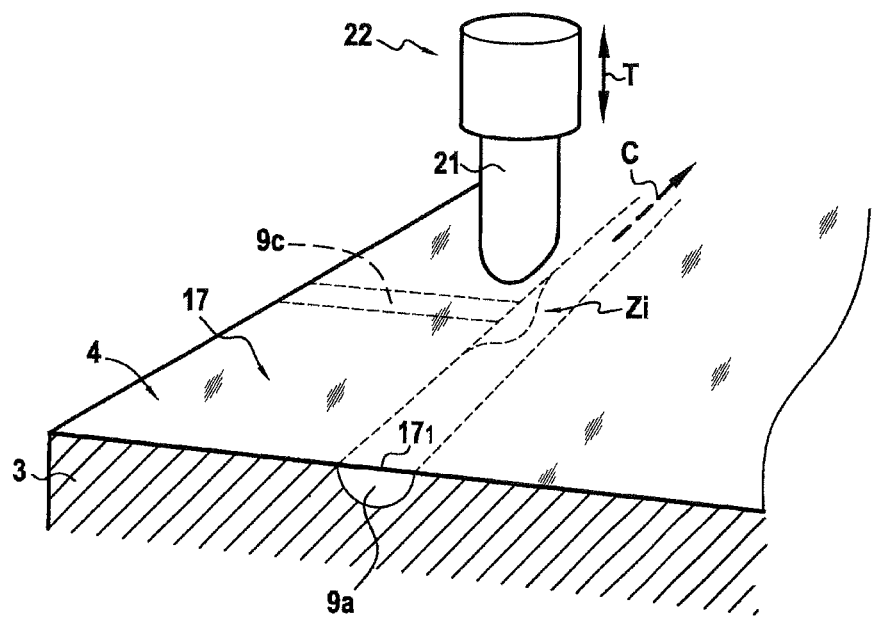
FIG. 6 is a schematic view of an exemplary application of the method according to the invention aiming at applying a force on the adhesive membrane of the test card along a direction perpendicular to the face of the test card.

In an exemplary embodiment illustrated in FIG. 6, the pressing member 21 may be driven in order to move closer/move away relatively to the test card 1 by means of an alternating linear displacement system of all types known per se. According to this alternative, the displacement system drives the sliding movement of the pressing member 21 along a direction T perpendicular to the face 4 or 5 of the test card 1. According to another exemplary embodiment, the test card 1 may be displaced so as to move closer/move away relatively to the pressing member 21 which remains fixed.

According to an advantageous alternative embodiment, the method according to the invention aims at exerting the force on the covering area $17_1$ of the adhesive membrane 17, simultaneously with a relative displacement between the test card 1 and the pressing member 21 along a direction parallel to the extension direction of the channel in order to allow adhesion of the covering area $17_1$ of the adhesive membrane 17 onto at least one portion of the length of said channel, superior to the supporting end of the pressing member 21.

As this emerges from FIG. 6, the pressing member 21 may have, in addition to the translational movement T, perpendicular to the face 4, 5 of the test card 1, a sliding movement C parallel to the face 4, 5 of the test card 1 and along the extension direction of the channel, i.e. according to an advantageous alternative embodiment, the length of a dissolution channel 9a.

Figure 7:
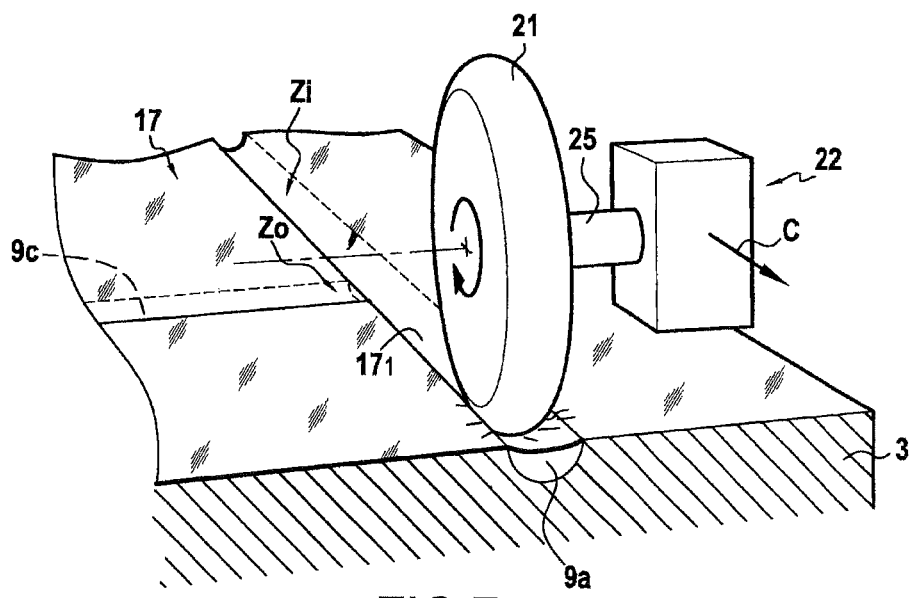
FIG. 7 is a schematic view of another exemplary application of the method according to the invention aiming at applying a force on the adhesive membrane of the test card, simultaneously with displacement of the application of the force along the extension direction of the channel.

FIG. 7 illustrates another alternative embodiment of a pressing member 21 mounted so as to be mobile in rotation around an axis of rotation 25 in order to roll on the bottom of the distribution channel 9a and along a portion of its direction taken along the extension direction C of the distribution channel 9a. According to this example, the pressing member 21 appears as a roller, the circumference of which has a rounded cross-section mating the section of the channel as indicated earlier.

According to a feature of the invention, it should be noted that the application of a force F on the adhesive membrane 17 coming into contact with the wall of the channel leads to displacement of the adhesive located in the application area of this force. It should be understood that the major portion of the adhesive 18 is displaced by the pressing member 21, in an obturation area Zo.

Thus, the displacement of the supporting member 21 along the extension direction C of the channels, as illustrated in FIG. 7, concomitantly leads to the displacement of the adhesive 18. Indeed, during the displacement of the pressing member 21 inside the channel, a portion of the adhesive is driven away or pushed by the pressing member 21 which acts like a roller-pressing member. The adhesive 18 is therefore established in at least one obturation area Zo adjacent to the isolation area Zi. It should be noted that in this isolation area Zi, the adhesive membrane 17 either adheres or not to the wall of the channel, what is important is that the adhesive driven away will obturate the channel upstream from the sample wells.

It should be noted that this roller-pressing effect may be obtained with a pressing member 21 exclusively displaced translationally T perpendicularly to a face of the test card 1. In this case, the adhesive 18 is driven on either side of the area of application of the pressing member 21, in the distribution channel 9a, or even in a filling channel 9c when the area of application of the force is located in this channel or at the intersection between a distribution channel 9a and a filling channel 9c.

The method according to the invention consists of selecting one or several locations of the covering area $17_1$ of the adhesive membrane 17, so as to create in a channel, an isolation area Zi and subsequently an obturation area Zo for at least one well 2 and preferably for each well 2, avoiding contamination between the whole of the wells of the card. These isolation areas Zi for the wells 2 may be made in any suitable locations of the distribution channels 9a and of the filling channels 9c in order to ensure isolation of the wells from each other. These isolation areas Zi extend over a more or less significant length of these channels.

According to a first alternative embodiment, provision may be made for producing an isolation area Zi on each filling channel 9c of a well 2.

According to a second embodiment, provision may be made for producing isolation areas Zi in the distribution channels 9a, at the intersection with the filling channels 9c and/or between two neighboring filling channels 9c opening into the distribution channel 9a.

According to a first exemplary embodiment, each isolation area Zi has a point-like nature in the sense that the portion of the covering area $17_1$ of the adhesive membrane 17 adhering to the wall of the channel has a limited surface area with respect to the length of the channel. FIG. 6 in a schematic and enlarged way, illustrates the making of an isolation area Zi with a point-like nature, by means of a pressing member 21 with limited length relatively to the length of the channel. The displacement movement of the pressing member 21 along the direction T gives the possibility of obtaining an isolation area Zi in the channel, at right angles to the pressing member. Such a movement of the pressing member 21 is capable of causing concomitant displacement of the adhesive 18 which may obturate a filling channel 9c which opens into the distribution channel 9a at right angles to the application of the supporting force. Of course, simultaneously producing several isolation areas Zi with as many pressing members 21 or successively with one or several pressing members 21 displaced in different locations of the test card 1, may be contemplated.

According to a second exemplary embodiment, the isolation area Zi has an extended nature. For this purpose, either the pressing member 21 has a supporting end of a large dimension, or the pressing member 21 is displaced relatively to the test card 1 along the extension direction C of the channel (FIG. 7).

According to a feature of the invention, the method according to the invention consists of producing an isolation area Zi over the length of the distribution channel 9a into which the filling channels 9c open. Advantageously, this isolation area Zi is continuous over the whole length into which open the filling channels 9c. The result is that all the wells 2 communicating with these filling channels 9c are isolated from each other.

According to an advantageous aspect of the invention, the method according to the invention gives the possibility, by means of the displacement of the pressing member 21 inside the distribution channels 9a, of obtaining concomitant displacement of the adhesive 18 in the filling channels 9c, opening into the distribution channels 9a. Thus, the test card 1 includes a continuous isolation area Zi on each distribution channel 9a, over the whole of its length, including intersections with the filling channels 9c in order to ensure their isolation. Further, each filling channel 9c includes an obturation area Zo provided with the adhesive 18, which is contiguous or adjacent with the obturation area Zo of the distribution channel 9a. Such an arrangement ensures inter-well isolation 2 insofar that the adhesive 18 will fill a section of the filling channels 9c.

It emerges from the foregoing description that regardless of the mode of application of the force on the adhesive membrane 17, in an isolation area Zi, this force according to the invention leads to displacement of the major portion of the volume of the adhesive located in this isolation area and on which the supporting member 21 acts. Advantageously, the force exerted on the adhesive membrane 17 is adapted so as to ensure the displacement of a volume of adhesive 18, greater than the volume of the obturation area Zo of the channel 9a, 9c in order to guarantee obturation of said channel with the displaced volume of adhesive 18. For example, the displaced volume of adhesive 18 is twice the volume of the channel to be obturated in order to obtain a hermetic seal of the channel.

It emerges from the foregoing description that the method according to the invention is simple to apply since it requires the application of a force on the covering area $17_1$ of the adhesive membrane 17 in order to allow its adhesion on the wall $9_1$ of the channel and displacement of the adhesive 18 driven away following application of this force. The support 3 does not undergo any deformation during the application of this force, giving the possibility of preserving the integrity of the sample wells. In the examples described above, application of this force is ensured via a pressing member 21 with a section mating the section of the channel. Of course, the displacement of the covering area $17_1$ of the adhesive membrane 17 may be ensured in a different way. For example, applying the supporting force on the covering area $17_1$ of the adhesive membrane 17 may be contemplated by means of an air jet.

According to an advantageous alternative, the obturation device 22 is applied within the scope of a processing machine for test cards 1 as for example described by U.S. Pat. No. 7,601,300; U.S. Pat. No. 5,798,085; U.S. Pat. No. 5,853,666 or U.S. Pat. No. 5,888,455.

Conventionally, a processing machine for test cards includes a succession of processing stations, i.e. notably a loading station, a station for identifying the test cards, a station for sealing the test card with respect to the outer environment, an incubation station and a station for reading test cards. Of course, such a machine includes conveying means allowing displacement of the test cards inside the stations and from one station to the other.

Advantageously, the phase for isolating the wells 2 by means of the method according to the invention is achieved during a translational movement of the test cards 1, performed just after the filling with the sample to be tested and prior to the reading station. Thus, during the displacement of the test cards 1, the translational movement of the test cards is used in order to allow, during a portion of this translational movement, the application of the pressing member 21 on the covering area $17_1$ of the adhesive membrane 17 so as to allow its adhesion on the wall of the distribution channel 9a. Thus, as the translational movement of the test cards 1 is parallel to the extension direction of the distribution channel 9a, the pressing member 21 may be rolled on the bottom of the distribution channel 9a along all or part of its length. The result is that the obturation phase of the wells 2 may be achieved in hidden time since it may occur during a translational movement of the test cards 1, performed by any conveying means with linear displacement, belonging to the processing machine. Thus, obturation of the wells 2 is simply obtained by fitting out the processing machine with an obturation device 22 according to the invention in proximity to conveying means belonging to the processing machine and ensuring translational movement to the test cards 1.

The invention is not limited to the described and illustrated examples since diverse modifications may be made thereto without departing from the scope thereof.

The invention claimed is:

1. An obturation device for applying a method for isolating at least one sample well (2) laid out in a test card (1) for analysis,
   wherein said test card includes a support (3) having at least one first main face (4, 5) from which is laid out at least one channel (9a, 9b, 9c) communicating with at least said well (2), the first face (4, 5) being coated with a membrane (17) provided with an adhesive (18) and which will cover said channel (9a, 9c), with a covering area ($17_1$),
   wherein the test card includes an isolation area for the sample well comprising a portion of a first channel and an obturation area for the sample well comprising a portion of a second channel, contiguous to the isolation area (Zi), which opens into the first channel at an intersection between the first channel and the second channel, wherein axes of the first and second channels are not aligned;
   and wherein the device includes a system (22) for exerting a force on at least one portion of a covering area ($17_1$) of the adhesive membrane (17) for displacing the membrane until causing the membrane to at least locally fit the shape of the wall ($9_1$) of a first channel (9a, 9c) so as to isolate said well (2) with respect to the channel by driving out the adhesive from the isolation area (Zi) of the first channel into the obturation area (Zo) of the second channel, by applying the force on the adhesive membrane.

2. The obturation device according to claim 1, characterized in that the system (22) for exerting a force includes a supporting member (21) with a section mating the section of the channel.

3. The obturation device according to claim 2, characterized in that the supporting member (21) has a rounded supporting end.

4. The obturation device according to claim 1, characterized in that the supporting member (21) is driven for moving closer/moving away relatively to the test card (1) in order to allow application of at least one portion of the covering area ($17_1$) of the adhesive membrane (17) on the wall ($9_1$) of the channel.

5. The obturation device according to claim 2, characterized in that the supporting member (21) is mounted so as to be mobile in rotation in order to roll on at least one portion of the length of the channel (9a, 9c).

6. A machine for processing test cards, characterized in that the machine includes an obturation device (22) according to claim 1).

7. The processing machine according to claim 6, characterized in that the machine includes a conveyor and processing stations, in that the conveyor is configured to displace test cards inside the processing stations and from one processing station to another processing station, and in than the obturation device (22) is mounted for acting on the test card (1) during a translational movement of the conveyor.

8. The obturation device according to claim 1, wherein the obturation device exerts force on the covering area of the adhesive membrane according to a pressure comprised between 0.3 and 0.7 kg/cm$^2$.

9. The obturation device according to claim 1, wherein the test card includes at least one fluid distribution channel communicating with an admission port and connected to said at least one well via at least one filling channel, and wherein the first channel is a distribution channel and the second channel is a filling channel.

10. The obturation device according to claim 1, wherein the test card includes at least one fluid distribution channel communicating with an admission port and connected to said at least one well via at least one filling channel, and wherein the first channel is a filling channel and the second channel is a distribution channel.

* * * * *